United States Patent [19]

Tazaki et al.

[11] Patent Number: 5,185,460
[45] Date of Patent: Feb. 9, 1993

[54] AMINOACETONITRILE DERIVATIVES

[75] Inventors: Seiji Tazaki; Nobuhiro Umeda; Nobuo Matsui; Tomio Yagihara; Katsunori Mikuma, all of Odawara, Japan

[73] Assignee: Nippon Soda Co., Ltd., Tokyo, Japan

[21] Appl. No.: 872,868

[22] Filed: Apr. 22, 1992

Related U.S. Application Data

[63] Continuation of Ser. No. 474,775, filed as PCT/JP89/00672 on Jul. 5, 1989, abandoned.

[51] Int. Cl.$^5$ .................. C07C 255/25; C07C 255/42
[52] U.S. Cl. ..................................... 558/392; 549/65; 549/460; 549/491; 558/256; 558/396; 558/426; 558/430; 558/438
[58] Field of Search ............... 558/396, 392, 256, 426, 558/430, 438; 549/65, 460, 491

[56] References Cited

FOREIGN PATENT DOCUMENTS 0135304 3/1985 European Pat. Off. .
0149324 7/1985 European Pat. Off. .

Primary Examiner—Joseph Paul Brust
Attorney, Agent, or Firm—Joseph C. Mason, Jr.; Ronald E. Smith

[57] ABSTRACT

Aminoacetonitrile derivatives, where the 2-position of aminoacetonitrile is optionally substituted by alkylthio groups, arylthio groups and heterocyclicthio groups. The process for making such compounds comprises reacting hydrogen cyanide with the desired corresponding R-S-H and recovering the crystallized salt thereof. The aminoacetonitrile derivatives are useful as starting materials to produce pharmaceutical and agricultural intermediates such as benzomide derivatives with fungicidal and herbicidal activities.

51 Claims, No Drawings

AMINOACETONITRILE DERIVATIVES

This application is a continuing application of copending application Ser. No. 07/474,775, filed as PCT/JP89/00672 on Jul. 5, 1989, now abandoned.

TECHNICAL FIELD

The present invention relates to new aminoacetonitrile derivatives where the 2-position of aminoacetonitrile is substituted by alkylthio groups, arylthio groups or heterocyclicthio groups.

The aminoacetonitrile derivatives of this invention can be used as starting materials for the manufacture of pharmaceutical and/or agricultural intermediates such as benzamide derivatives with fungicidal and herbicidal activities as shown in EP-135304.

They can also be used as starting materials for the manufacture of dyes, perfumes, polymers, and so on.

BACKGROUND ART

α-substituted aminoacetonitrile derivatives are usually prepared via 3 steps: aminoacetonitrile, prepared by the reaction of hydrogen cyanide with formaldehyde, followed by treatment with excess of ammonia, is acylated for the protection of amino group, and then halogenated to give α-halo-acylaminoacetonitrile which is allowed to react with nucleophiles such as alcohol, thiol or amine to give an aimed compound. However, α-substituted aminoacetonitrile is not obtained by this method because hydrolysis of α-substituted acylaminoacetonitrile may be difficult.

The purpose of this invention is to provide new and stable aminoacetonitrile derivatives and their salts which can be used as starting materials for various types of organic compounds, and furthermore their inexpensive synthetic methods.

DISCLOSURE OF INVENTION

Broadly, this invention provides an aminoacetonitrile derivative having the formula

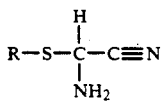

wherein: R is selected from
(1) alkyl,
(2) optionally substituted alkyl in which one or more substituent(s) is selected from
 (a) phenyl
 (b) optionally substituted phenyl in which one or more substituents is selected from
  (i) halogen, and,
  (ii) $C_{1-3}$ alkyl,
 (c) $C_{1-3}$ alkoxycarbonyl
 (d) hydroxy,
 (e) mercapto,
 (f) halogen,
 (g) naphthyl,
 (h) furyl, and,
 (i) a group having the formula $R_1NCHO-$ wherein $R_1$ is selected from
  (i) phenyl,
  (ii) optionally substituted phenyl in which one or more substituent(s) is selected from
   (A) halogen,
   (B) alkyl,
   (C) optionally substituted alkyl in which one or more substituent(s) is selected from
    (aa) phenyl, and,
    (bb) cycloalkyl,
(3) phenyl,
(4) optionally substituted phenyl in which one or more substituent(s) is selected from
 (a) halogen,
 (b) $C_{1-5}$ alkyl
 (c) optionally substituted $C_{1-5}$ alkyl in which one or more substituent(s) is selected from
  (i) halogen, and,
  (ii) phenyl,
 (d) cycloalkyl,
 (e) phenyl,
 (f) halophenyl,
 (g) phenoxy,
 (h) optionally substituted phenoxy in which one or more substituent(s) is selected from
  (i) $C_{1-3}$ alkyl, and,
  (ii) haloalkyl,
 (i) tetrahydronaphthoxy,
 (j) $C_{1-3}$ alkoxy
 (k) haloalkoxy
 (l) nitro,
 (m) amino, and,
 (n) hydroxy,
(5) cycloalkyl,
(6) $C_{2-4}$ alkenyl,
(7) naphthyl,
(8) halonaphthyl,
(9) dibenzofaranyl,
(10) $C_{1-3}$ alkylcarbonyl,
(11) thienyl, and,
(12) fluorenyl; or,
an acceptable salt thereof.

The present invention also provides a process for the preparation of such novel compounds.

More specifically the present invention also provides a compound represented by the structural formula (I):

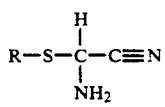 (I)

wherein: R is selected from
(1) $C_{1-12}$ alkyl;
(2) optionally substituted $C_{1-12}$ alkyl in which one or more substituent(s) is selected from
 (a) phenyl,
 (b) optionally substituted phenyl in which one or more substituent(s) is selected from
  (i) 1 to 3 halogen atoms, and,
  (ii) $C_{1-3}$ alkyl
 (c) $C_{1-3}$ alkoxycarbonyl
 (d) hydroxy,
 (e) mercapto,
 (f) halogen,
 (g) naphthyl,
 (h) furyl,
 (i) phenylcarbamoyl, (j) substituted phenylcarbamoyl in which the substituent is halogen,
(k) $C_{1-12}$ alkylcarbamoyl, and,
(l) optionally substituted $C_{1-12}$ alkylcarbamoyl in which the substituents are from 1 to 2 phenyl;
(3) phenyl;
(4) optionally substituted phenyl in which one or more substituent(s) is selected from
  (a) 1 to 3 halogen atoms,
  (b) $C_{1-5}$ alkyl,
  (c) substituted $C_{1-2}$ alkyl in which the substituent is halogen,
  (d) phenyl,
  (e) substituted phenyl in which the substituent is halogen,
  (f) $C_{1-3}$ alkylsubstituted phenoxy,
  (g) $C_{1-3}$ haloalkylsubstituted phenoxy,
  (h) tetrahydronaphthoxy,
  (i) $C_{1-3}$ alkoxy,
  (j) substituted $C_{1-3}$ alkoxy in which the substituent is halogen,
  (k) amino,
  (l) nitro, and
  (m) hydroxy;
(5) $C_{5-7}$ cycloalkyl;
(6) substituted $C_{5-7}$ cycloalkyl in which the substituent is phenyl;
(7) $C_{2-4}$ alkenyl;
(8) naphthyl;
(9) substituted naphthyl in which the substituent is halogen;
(10) dibenzofuranyl;
(11) $C_{1-3}$ alkylcarbonyl;
(12) thienyl, and,
(13) fluorenyl; or
an acceptable salt thereof.

Compounds of this invention may be produced from a process comprising reacting hydrogen cyanide with a compound having the formula $$R\text{—}S\text{—}H$$

wherein R is selected from the groups defined as aforesaid.

The aminoacetonitrile derivative represented by the above general formula (I) can be generally isolated as crystal of salts such as p-toluenesulfonate or hydrochloride.

These salts exist extremely stable, and can be purified by ordinary methods such as recrystallization.

BEST MODE FOR CARRYING OUT THE INVENTION

The aminoacetonitrile derivatives having the formula (I) can be manufactured by the following processes
(1) Manufacturing process A

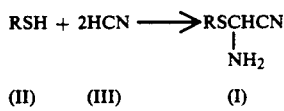

(II)    (III)    (I)

The reaction is carried out in organic solvents in the presence of a base at 0° C. to 40° C. for 30 minutes to several hours, and, after usual work-up, an acid including an organic acids such as oxalic acid, organic sulfonic acids such as p-toluenesulfonic acid and naphthalene sulfonic acid, or inorganic acids such as hydrochloric acid, sulfuric acid or phosphoric acid, is added to the resulting organic layer to isolate an aminoacetonitrile derivative as the salt of the acid used.

An appropriate thiol is used depending on the aimed compound.

Reaction solvents used include hydrocarbons such as benzene, toluene and xylene, nitriles such as acetonitrile, halogenated hydrocarbons such as chloroform and methylene chlorides, esters such as ethyl acetate, and alcohols such as ethanol. These can be used as mixture.

For the base, inorganic basic compounds such as sodium carbonate and organic basic compounds such as triethylamine, diethylamine and diazabicycloundecene (DBU) may be used.

A range of molar concentration (mol) of each component is generally 1 for Compound (II), 2-20, preferably 4-8 for Compound (III) and 0.1-2, preferably 0.2-0.6 for the base.

The reaction is usually carried out under the atmospheric pressure, though media used, types of solvents, etc and amount used may differ depending on purpose. The salt of aminoacetonitrile derivatives isolated from the reaction solution is reacted with alkali to easily isolate free intended compounds, which, if necessary, can be purified by column chromatography.

(2) Manufacturing process B

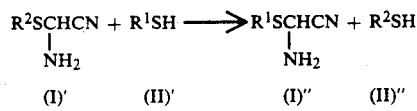

(I)'    (II)'    (I)"    (II)"

wherein $R^1$ represents an alkyl group which may be substituted by phenyl groups (which may be substituted by halogen atoms or $C_{1-3}$ alkyl groups), $C_{1-3}$ alkoxy-carbonyl groups, hydroxy groups, mercapto groups, halogen atoms, naphthyl groups, furyl groups or $R_1NHCO$— groups (where $R_1$ is a phenyl group which may be substituted by halogen atoms, an alkyl group which may be substituted by phenyl groups or a cycloalkyl group), a cycloalkyl group, or a $C_{2-4}$ alkenyl group; $R^2$ represents a phenyl group which may be substituted by halogen atoms, $C_{1-5}$ alkyl groups (which may be substituted by halogen atoms or phenyl groups), cycloalkyl groups, phenyl groups (which may be substituted by halogen atoms), phenoxy groups (which may be substituted by $C_{1-3}$ alkyl groups or haloalkyl groups), tetrahydronaphthoxy groups, $C_{1-3}$ alkoxy groups (which may be substituted halogen atoms), nitro groups, amino groups or hydroxy groups, a naphthyl group which may be substituted by halogen atoms, a thienyl group or a fluorenyl group.

The reaction is carried out in organic solvents in the presence of a base at 0° C. to 80° C. for 30 minutes to several hours.

For the organic solvents and the base, the items specified for the manufacturing process A can be used.

After the reaction are completed, the similar procedures operated under the manufacturing process A are carried out to obtain salts or free forms of intended products.

The structure of the product was determined by such means as NMR, IR, Mass spectra and elemental analysis, and, if necessary, by leading to the known compound.

The present invention is described in detail by using examples. The scope of the invention, however, is by no means limited by these examples.

EXAMPLE 1

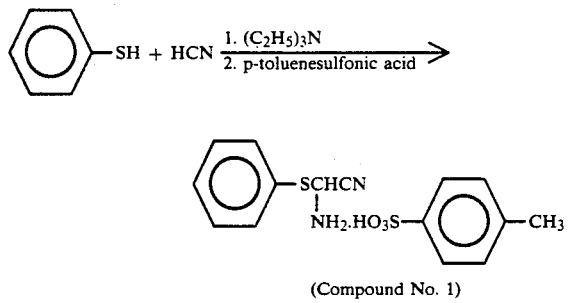

(Compound No. 1)

In a 500 ml flask were placed thiophenol (17.4 g), triethylamine (8.0 g) and benzene (150 ml).

Liquid hydrogen cyanide (25.6 g) was added to this solution at 5° C. and stirring was continued at 20° C. for 1.5 hours.

Then p-toluenesulfonic acid monohydrate (30.0 g) was added to the reaction mixture and stirring was continued at 0°-5° C. for 10 minutes. The white precipitate was filtered, washed with diethyl ether (20 ml) and acetonitrile (20 ml) and dried in a vacuum desiccator.

Phenylthioaminoacetonitrile p-toluenesulfonate (38.0 g) was obtained in a yield of 71.5% m.p. 145°-146° C.

EXAMPLE 2

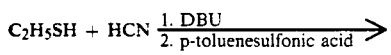

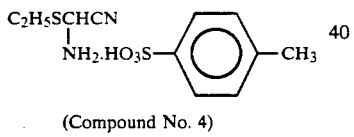

(Compound No. 4)

In a 100 ml flask were placed ethanthiol (2.5 g), DBU (3.0 g) and acetonitrile (40 ml).

Liquid hydrogen cyanide (6.5 g) was added to this solution at 5° C. and stirring was continued at 20° C. for 3 hours. The reaction mixture was poured into 10% sodium hydroxide (60 g) which was precooled at 5° C. in 300 ml glass vessel, followed by extracting with chloroform (20 ml) twice. The chloroform layer was dried over anhydrous magnesium sulfate.

p-Toluenesulfonic acid monohydrate (7.6 g) was added to the dried chloroform layer and stirring was continued at 0°-5° C. for 10 minutes. The white precipitate was filtered, washed with diethyl ether (10 ml) and acetonitrile (10 ml) dried in a vacuum desiccator.

Ethylthioaminoacetonitrile p-toluenesulfonate (4.9 g) was obtained in a yield of 40.0%. m.p. 125°-126° C.

EXAMPLE 3

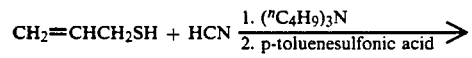

-continued

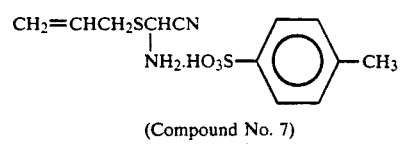

(Compound No. 7)

In a 100 ml flask were placed allyl mercaptan (2.2 g), tri-n-Buthyl amine (1.9 g) and dichloromethane (20 ml). Liquid hydrogen cyanide (3.3 g) was added to this solution at 5° C. and stirring was continued at 20° C. for 1.5 hours.

When worked up as Example 1, allylthioaminoacetonitrile p-toluenesulfonate (3.1 g) was obtained in a yield of 48.7%. m.p. 127°-129° C.

EXAMPLE 4

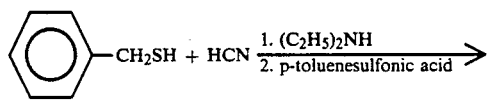

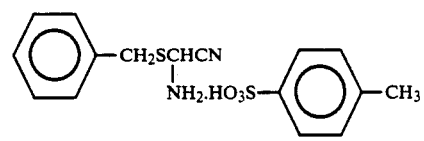

(Compound No. 8)

In a 100 ml flask were placed benzyl mercaptan (2.5 g), diethyl amine (0.8 g) and xylene (20 ml).

Liquid hydrogen cyanide (3.3 g) was added to this solution at 5° C. and stirring was continued at 20° C. for 1 hour. When worked up as Example 1, benzylthioaminoacetonitrile p-toluenesulfonate (3.3 g) was obtained in a yield of 45.0%. m.p. 143°-144° C.

EXAMPLE 5

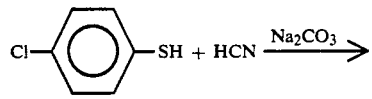

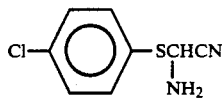

(Compound No. 25)

In a 100 ml flask were placed p-chlorothiophenol (2.9 g), 20% sodium carbonate (10.6 g) and acetonitrile (20 ml). Liquid hydrogen cyanide (3.3 g) was added to this solution at 10° C. and stirring was continued at 20° C. for 3 hours. The reaction mixture was poured into 10% sodium hydroxide (30 g) which was precooled at 5° C. in 300 ml glass vessel, followed by extracting with chloroform (20 ml) twice.

The chloroform layer was dried over anhydrous magnesium sulfate. The residue left after the evaporation of chloroform was purified by column chromatography. p-Chlorophenylthioamino acetonitrile (1.7 g) was obtained in a yield of 42.9%. m.p. 74°-76° C.

EXAMPLE 6

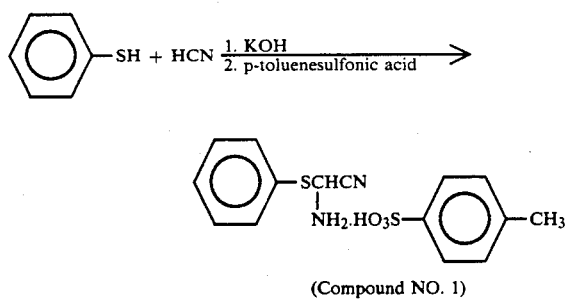

(Compound NO. 1)

In a 100 ml flask were placed thiophenol (2.2 g), potassium hydroxide (0.6 g) and ethyl alcohol (30 ml).

Liquid hydrogen cyanide (3.3 g) was added to this solution at 5° C. and stirring was continued at 20° C. for 2 hours. The reaction mixture was poured into 10% sodium hydroxide (30 g) which was precooled at 5° C. in 300 ml glass vessel, followed by extracting with chloroform (20 ml) twice. The chloroform layer was dried over anhydrous magnesium sulfate.

When worked up as Example 2, phenylthioaminoacetonitrile p-toluenesulfonate (3.1 g) was obtained in a yield of 45.4%.

EXAMPLE 7

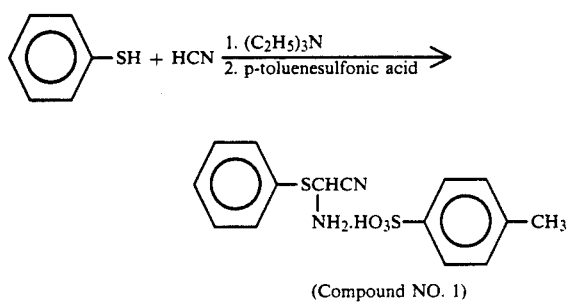

(Compound NO. 1)

In a 100 ml flask were placed thiophenol (2.2 g), triethylamine (1.0 g) and ethylacetate (15 ml).

Liquid hydrogen cyanide (3.3 g) was added to this solution at 5° C. and stirring was continued at 20° C. for 2.5 hours. The reaction mixture was poured into 10% sodium hydroxide (30 g) which was precooled at 5° C. in 300 ml glass vessel, followed by extracting with chloroform (20 ml) twice. The chloroform layer was dried over anhydrous magnesium sulfate. When worked up as Example 2, phenylthioaminoacetonitrile p-toluenesulfonate (3.4 g) was obtained in a yield of 51.0%.

EXAMPLE 8

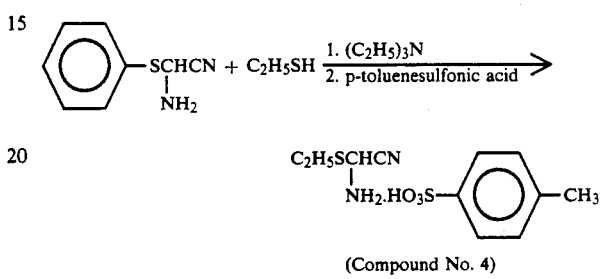

(Compound No. 4)

In a 100 ml flask were placed phenylthioaminoacetonitrile (6.6 g), triethylamine (0.8 g) and acetonitrile (30 ml). Ethylmercaptan (1.5 g) was added to this solution at 15° C. and stirring was continued at 20° C. for 12 hours. To the residue left after the evaporation of acetonitrile and triethylamine, dichloromethane (10 ml) and p-toluenesulfonic acid monohydrate (7.6 g) were added. Then the reaction mixture stirred at 0°–5° C. for 10 minutes. The white precipitate was filtered, washed with diethyl ether (20 ml) and acetonitrile (20 ml) and dried in a vacuum desiccator.

Ethylthioaminoacetonitrile p-toluenesulfonate (9.4 g) was obtained in a yield of 69.6%.

Inclusive of the above, each compound with the scope of the present invention which can be prepared in analogous method is tabulated in Table 1.

TABLE 1

Structure $$\underset{NH_2}{\underset{|}{RSCHCN}}$$

| Compound NO. | R | salt | ( ) m.p. °C. |
|---|---|---|---|
| 1 | C₆H₅– (phenyl) | CH₃–C₆H₄–SO₃H | (145–146) |
| 2 | Cl–C₆H₄– | " | (149–150) |
| 3 | H₃C–C₆H₄– | " | (153–155) |
| 4 | $C_2H_5-$ | " | (125–126) |

TABLE 1-continued

Structure
$$\underset{\underset{NH_2}{|}}{RSCHCN}$$

| Compound NO. | R | salt | ( ) m.p. °C. |
|---|---|---|---|
| 5 | cyclohexyl-H | " | (137–139) |
| 6 | $CH_3(CH_2)_7-$ | " | (120–122) |
| 7 | $CH_2=CHCH_2-$ | " | (127–129) |
| 8 | phenyl-$CH_2-$ | " | (143–144) |
| 9 | Br-phenyl- | " | (157–158.5) |
| 10 | Cl-phenyl-$CH_2-$ | " | (159–160.5) |
| 11 | naphthyl- | " | (155–156.5) |
| 12 | F-biphenyl- | " | (156–158) |
| 13 | $H_3C$-phenyl-$CH_2-$ | " | (152–153) |
| 14 | $H_3C$-phenyl-O-phenyl- | " | (147–148) |
| 15 | dibenzofuranyl- | " | (160–161) |
| 16 | F-naphthyl- | " | (161–162) |
| 17 | $CH_3O$-phenyl- | " | (154–155) |
| 18 | $\underset{\underset{O}{\parallel}}{CH_3OCCH_2CH_2-}$ | " | (99–100) |
| 19 | $CH_3(CH_2)_{11}-$ | " | (119–120.5) |

TABLE 1-continued
Structure
$$\underset{NH_2}{RSCH\underset{|}{C}N}$$
| Compound NO. | R | salt | ( ) m.p. °C. |
|---|---|---|---|
| 20 | CH$_3$— | " | (134–135) |
| 21 | 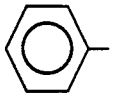 | HCl | (115–117) |
| 22 | " | H$_2$SO$_4$ | (84–85) |
| 23 | " | (COOH)$_2$ | (99–100) |
| 24 | " | — | N$_D^{20}$ 1.5955 |
| 25 | 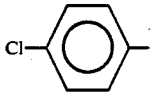 4-Cl-C$_6$H$_4$— | — | (74–76) |
| 26 | 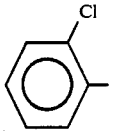 2-Cl-C$_6$H$_4$— | CH$_3$-C$_6$H$_4$-SO$_3$H | (147–148) |
| 27 | 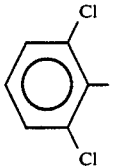 2,3-Cl$_2$-C$_6$H$_3$— | " | |
| 28 | 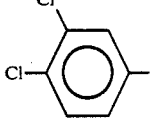 3,4-Cl$_2$-C$_6$H$_3$— | " | (162–163) |
| 29 | 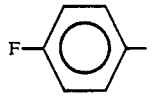 4-F-C$_6$H$_4$— | " | (159–161) |
| 30 | 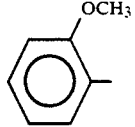 2-OCH$_3$-C$_6$H$_4$— | " | |
| 31 | 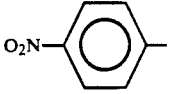 4-O$_2$N-C$_6$H$_4$— | " | |
| 32 | 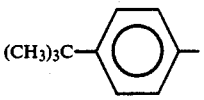 4-(CH$_3$)$_3$C-C$_6$H$_4$— | — | N$_D^{26}$ 1.5608 |
| 33 | 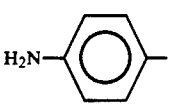 4-H$_2$N-C$_6$H$_4$— | CH$_3$-C$_6$H$_4$-SO$_3$H | (146–147) |

TABLE 1-continued

Structure:
$$\underset{\underset{NH_2}{|}}{RSCHCN}$$

| Compound NO. | R | salt | ( ) m.p. °C. |
|---|---|---|---|
| 34 | C₆H₅-NHCOCH₂- | " | (223-225) |
| 35 | Cl-C₆H₄-NHCOCH₂- | " | |
| 36 | CH₃(CH₂)₃NHCOCH₂- | " | |
| 37 | C₆H₁₁(H)-CHCOCH₂- | " | |
| 38 | CH₃(CH₂)₁₁NHCOCH₂ | " | |
| 39 | C₆H₅-CH₂NHCOCH₂- | " | |
| 40 | HOCH₂CH₂- | " | |
| 41 | ClCH₂CH₂CH₂- | " | (140-141) |
| 42 | CH₃(CH₂)₃- | " | (145-146) |
| 43 | CH₃CH₂CH₂- | " | (138-139) |
| 44 | CH₃CO- | " | |
| 45 | (furan-2-yl)-CH₂- | " | (136-138) |
| 46 | (thiophen-2-yl) | " | (153-155) |
| 47 | CF₃-C₆H₄- | " | (149-151) |
| 48 | HO-C₆H₄- | " | (164-165) |
| 49 | CF₃O-C₆H₄- | " | |
| 50 | HSCH₂CH₂- | " | (120-122) |
| 51 | fluorenyl | " | (159-161) |
| 52 | 2-F-C₆H₄- | " | (130-131) |

TABLE 1-continued

Structure
$$\text{RSCHCN} \atop |\atop \text{NH}_2$$

| Compound NO. | R | salt | ( ) m.p. °C. |
|---|---|---|---|
| 53 | 4-I-C₆H₄– | " | (152–153) |
| 54 | 3-Cl-4-F-C₆H₃– | " | (150–151) |
| 55 | 2-biphenyl | " | (119–120) |
| 56 | 2,4-F₂-C₆H₃– | " | (153–155) |
| 57 | 4-(phenoxy)-C₆H₄– | " | (123–125) |
| 58 | 1-naphthyl-CH₂– | " | (145–147) |
| 59 | 4-(5,6,7,8-tetrahydronaphth-2-yloxy)-C₆H₄– | " | (150–151) |
| 60 | 3-Br-C₆H₄– | " | (144–145) |
| 61 | 4-(4-CF₃-phenoxy)-C₆H₄– | " | (158–160) |

TABLE 1-continued

Structure
RSCHCN
|
NH$_2$

| Compound NO. | R | salt | ( ) m.p. °C. |
|---|---|---|---|
| 62 | 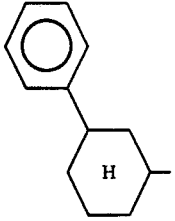 | " | (130–132) |
| 63 | 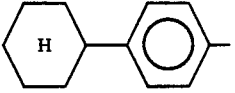 | " | (148–149) |
| 64 | 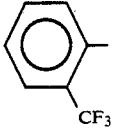 | " | (138–139) |
| 65 |  | — | N$_D^{26}$ 1.4928 |
| 66 | " | (COOH)$_2$ | (111–112) |
| 67 | 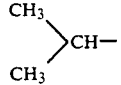 | — | N$_D^{26}$ 1.5586 |
| 68 | 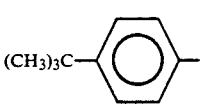 | (COOH)$_2$ | (99–100) |

INDUSTRIAL APPLICABILITY

The aminoacetonitrile derivatives of this invention, which are compounds substituted at the 2-position with RS— group, can be isolated stably. The derivatives are very reactive and react with various reagents to give useful products, being useful as synthetic materials for intermediates of such as pharmaceutical, agricultural chemicals, dyes, perfumes and polymers. In addition, the derivatives can be synthesized directly from hydrogen cyanide under mild conditions as described in the aforementioned examples and thus prepared at a low cost, having extremely great industrial significance.

What is claimed is:

1. A compound represented by the structural formula (I):

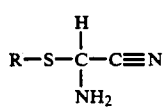

wherein: R is selected from
(1) C$_{1-12}$ alkyl,
(2) optionally substituted C$_{1-12}$ alkyl in which one or more substituent(s) is selected from
  (a) phenyl
  (b) optionally substituted phenyl in which one or more substituent(s) is selected from
    (i) 1 to 3 halogen atoms, and,
    (ii) C$_{1-3}$ alkyl,
  (c) C$_{1-3}$ alkoxycarbonyl
  (d) hydroxy,
  (e) mercapto,
  (f) halogen,
  (g) naphthyl,
  (h) furyl,
  (i) phenylcarbamoyl,
  (j) substituted phenylcarbamoyl in which the substituent is halogen,
  (k) C$_{1-12}$ alkylcarbamoyl, and,
  (l) optionally substituted C$_{1-12}$ alkylcarbamoyl in which the substituents are from 1 to 2 phenyl;
(3) phenyl;
(4) optionally substituted phenyl in which one or more substituent(s) is selected from
  (a) 1 to 3 halogen atoms,
  (b) C$_{1-5}$ alkyl, (c) substituted $C_{1-2}$ alkyl in which the substituent is halogen,
(d) phenyl,
(e) substituted phenyl in which the substituent is halogen,
(f) $C_{1-3}$ alkylsubstituted phenoxy,
(g) $C_{1-3}$ haloalkylsubstituted phenoxy,
(h) tetrahydronaphthoxy,
(i) $C_{1-3}$ alkoxy,
(j) substituted $C_{1-3}$ alkoxy in which the substituent is halogen,
(k) amino,
(l) nitro, and
(m) hydroxy;
(5) $C_{5-7}$ cycloalkyl;
(6) substituted $C_{5-7}$ cycloalkyl in which the substituent is phenyl;
(7) $C_{2-4}$ alkenyl;
(8) naphthyl;
(9) substituted naphthyl in which the substituent is halogen;
(10) dibenzofuranyl;
(11) $C_{1-3}$ alkylcarbonyl;
(12) thienyl, and,
(13) fluorenyl; or
an acceptable sat thereof.

2. Process for preparing a compound according to claim 1 which comprises reacting hydrogen cyanide with a compound having the formula $$R-S-H$$

wherein R is selected from the group(s) defined in claim 1 specified.

3. Process according to claim 2 wherein the reaction takes place in the presence of a solvent at a temperature from 0° C. to 40° C. and a reaction time from 30 to 720 minutes.

4. Process according to claim 3 wherein an organic acid is added to the reaction products thereby converting the aminoacetonitrile derivative to a crystallized salt of such acid.

5. Compound No. 1 of Table 1 according to claim 1.
6. Compound No. 2 of Table 1 according to claim 1.
7. Compound No. 3 of Table 1 according to claim 1.
8. Compound No. 8 of Table 1 according to claim 1.
9. Compound No. 9 of Table 1 according to claim 1.
10. Compound No. 10 of Table 1 according to claim 1.
11. Compound No. 11 of Table 1 according to claim 1.
12. Compound No. 12 of Table 1 according to claim 1.
13. Compound No. 13 of Table 1 according to claim 1.
14. Compound No. 14 of Table 1 according to claim 1.
15. Compound No. 16 of Table 1 according to claim 1.
16. Compound No. 17 of Table 1 according to claim 1.
17. Compound No. 21 of Table 1 according to claim 1.
18. Compound No. 22 of Table 1 according to claim 1.
19. Compound No. 23 of Table 1 according to claim 1.
20. Compound No. 24 of Table 1 according to claim 1.
21. Compound No. 25 of Table 1 according to claim 1.
22. Compound No. 26 of Table 1 according to claim 1.
23. Compound No. 27 of Table 1 according to claim 1.
24. Compound No. 28 of Table 1 according to claim 1.
25. Compound No. 29 of Table 1 according to claim 1.
26. Compound No. 30 of Table 1 according to claim 1.
27. Compound No. 31 of Table 1 according to claim 1.
28. Compound No. 32 of Table 1 according to claim 1.
29. Compound No. 33 of Table 1 according to claim 1.
30. Compound No. 34 of Table 1 according to claim 1.
31. Compound No. 35 of Table 1 according to claim 1.
32. Compound No. 39 of Table 1 according to claim 1.
33. Compound No. 47 of Table 1 according to claim 1.
34. Compound No. 48 of Table 1 according to claim 1.
35. Compound No. 49 of Table 1 according to claim 1.
36. Compound No. 51 of Table 1 according to claim 1.
37. Compound No. 52 of Table 1 according to claim 1.
38. Compound No. 53 of Table 1 according to claim 1.
39. Compound No. 54 of Table 1 according to claim 1.
40. Compound No. 55 of Table 1 according to claim 1.
41. Compound No. 56 of Table 1 according to claim 1.
42. Compound No. 57 of Table 1 according to claim 1.
43. Compound No. 58 of Table 1 according to claim 1.
44. Compound No. 59 of Table 1 according to claim 1.
45. Compound No. 60 of Table 1 according to claim 1.
46. Compound No. 61 of Table 1 according to claim 1.
47. Compound No. 62 of Table 1 according to claim 1.
48. Compound No. 63 of Table 1 according to claim 1.
49. Compound No. 64 of Table 1 according to claim 1.
50. Compound No. 68 of Table 1 according to claim 1.

51. A process for the preparation of an aminoacetonitrile derivative or salts thereof having the formula $$\text{R}^1\text{SCHCN}$$
$$|$$
$$\text{NH}_2$$

which comprises reacting a compound or salts thereof having the formula $$\text{R}^2\text{SCHCN}$$
$$|$$
$$\text{NH}_2$$

with a thiol compound having the formula $$\text{R}^1\text{SH}$$

wherein $R^1$ represents an alkyl groups which may be substituted by phenyl groups (which may be substituted by halogen atoms or $C_{1-3}$ alkyl groups), $C_{1-3}$ alkoxycarbonyl groups, hydroxy groups, mercapto groups, halogen atoms, naphthyl groups, furyl groups or $R_1\text{NHCO}—$ groups (where $R_1$ is a phenyl groups which may be substituted by halogen atoms, an alkyl groups which may be substituted by phenyl groups or a cycloalkyl group), a cycloalkyl group, or a $C_{2-4}$ alkenyl group; $R^2$ represents a phenyl group which may be substituted by halogen atoms, $C_{1-5}$ alkyl groups (which may be substituted by halogen atoms or phenyl groups), cycloalkyl groups, phenyl groups (which may be substituted by halogen atoms), phenoxy groups (which may be substituted by $C_{1-3}$ alkyl groups or haloalkyl groups), tetrahydronaphthoxy groups, $C_{1-3}$ alkoxy groups (which may be substituted halogen atoms), nitro groups, amino groups or hydroxy groups, a naphthyl group which may be substituted by halogen atoms, a thienyl group or a fluorenyl group.

* * * * *